United States Patent [19]

Prescott

[11] Patent Number: 5,514,126
[45] Date of Patent: May 7, 1996

[54] FIBER OPTIC ASSEMBLY FOR LASER TREATMENT SYSTEM

[76] Inventor: Marvin Prescott, 833 Moraga Dr., Suite 15, Los Angeles, Calif. 90049

[21] Appl. No.: 136,382

[22] Filed: Oct. 12, 1993

[51] Int. Cl.⁶ .................................................. A61B 17/36
[52] U.S. Cl. .................................................. 606/10; 606/16
[58] Field of Search .................................. 257/916, 914; 606/10, 11, 12, 15, 16, 1, 14

[56] References Cited

U.S. PATENT DOCUMENTS

| | | | |
|---|---|---|---|
| 3,327,712 | 6/1967 | Kaufman et al. | 128/398 |
| 4,517,974 | 5/1985 | Tanner | 606/16 |
| 4,538,609 | 9/1985 | Takenaka et al. | 128/303 |
| 4,576,160 | 3/1986 | Tanaka | 128/303 |
| 4,660,925 | 4/1987 | McCcaugham, Jr. | 350/96 |
| 4,669,467 | 6/1987 | Willett et al. | 128/303 |
| 4,744,624 | 5/1988 | Burston | 350/96 |
| 4,848,339 | 7/1989 | Rink et al. | 128/303 |
| 4,860,172 | 8/1989 | Schlager et al. | 362/32 |
| 5,029,970 | 7/1991 | Hengst et al. | 606/10 |
| 5,142,598 | 8/1992 | Tabone | 385/78 |
| 5,163,935 | 11/1992 | Black et al. | 606/17 |
| 5,188,632 | 2/1993 | Goldenberg | 606/7 |
| 5,221,279 | 6/1993 | Cook et al. | 606/15 |
| 5,267,993 | 12/1993 | Grace et al. | 606/15 |

Primary Examiner—Stephen C. Pellegrino
Assistant Examiner—Sonya Harris-Ogugua
Attorney, Agent, or Firm—Graham & James

[57] ABSTRACT

A laser treatment system includes a fiber optic assembly for conducting laser beam from a laser beam source to a patient's body. The fiber optic assembly is disposable, sterilized and includes a safety switch to prevent inadvertent application of power to the laser beam generation circuit, thereby preventing accidental generation of a laser beam without a fiber optic assembly in place to guide the laser beam.

22 Claims, 5 Drawing Sheets

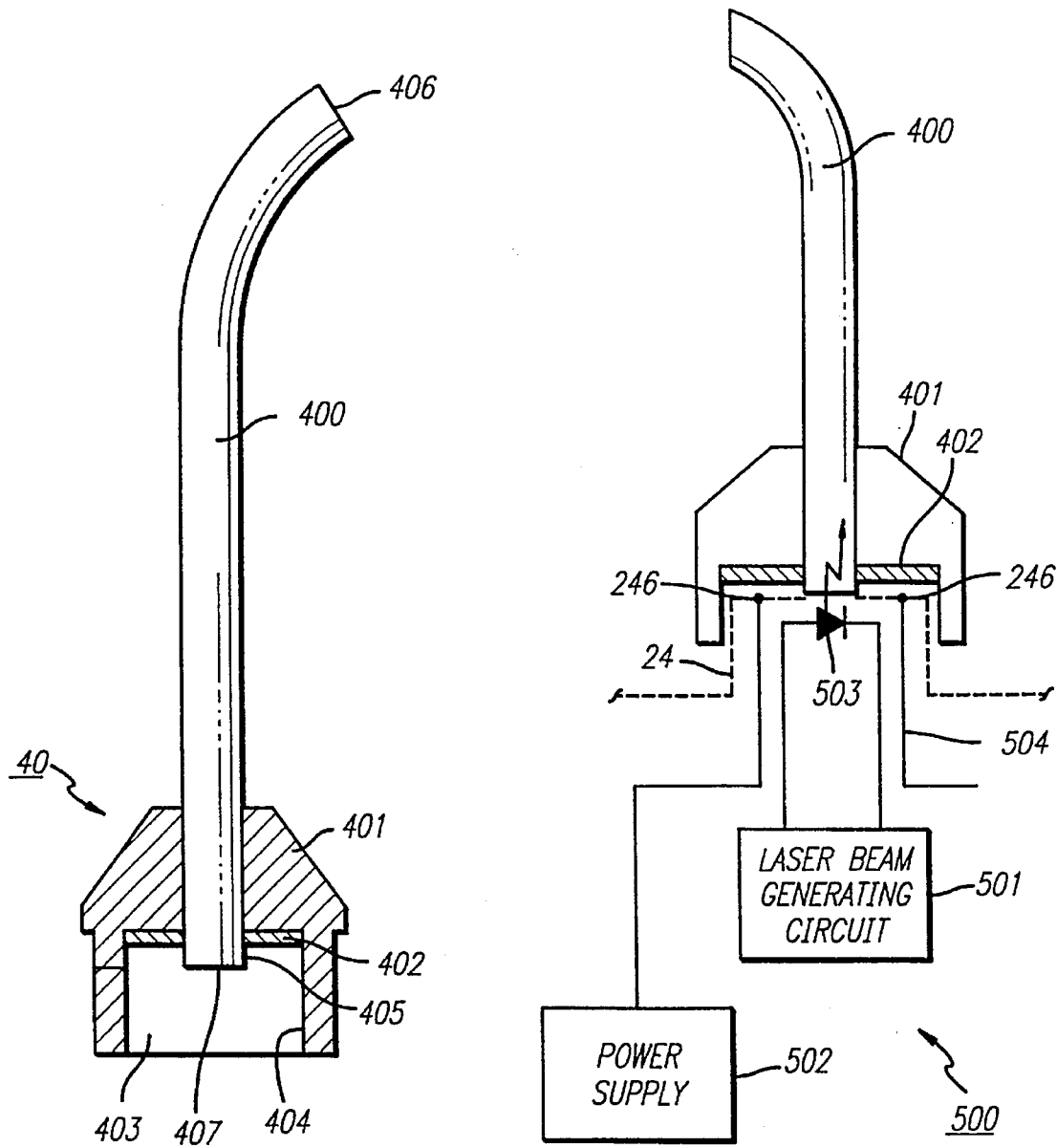

ated and the individual stares directly into the beam. Prior art
FIBER OPTIC ASSEMBLY FOR LASER TREATMENT SYSTEM

FIELD OF THE INVENTION

The present invention is directed to a system for applying laser beam energy in the treatment of medical conditions. More particularly, the present invention is directed to a fiber optic assembly for a laser treatment system for applying the energy from a laser beam to a subject undergoing treatment in a cost effective and efficient manner.

BACKGROUND OF THE INVENTION

Low power lasers, e.g., lasers having an energy output on the order of one milliwatt to 100 milliwatts and varying wavelengths (e.g., 630 nM–904 nM), have been used since 1969 for medical and dental applications which vary from pain control, wound healing, nerve stimulation, reduction of edema, and stimulation of the body's neurotransmitter and neurohormone systems. Low power lasers have also been extensively used in veterinary medicine particularly in the treating of bowed tendons in race horses. However, there are a number of difficulties associated with utilizing relatively sophisticated laser technology in the treatment of medical conditions in humans and animals.

One of the problems with prior art laser systems is they do not provide a sterilized device for each patient to be treated. Since it is quite common for a doctor to see a large number of patients in a given day, this requires constant sterilization and re-sterilization of the instrument being used. Sterilization is not effective in eliminating bacteria and viruses one hundred percent of the time. Accordingly, there is still a risk of transmission of the AIDS virus, hepatitis, herpes, etc.

One of the ways medical instruments such as laser applicators are sterilized is through what is known as an autoclaving process. This process typically subjects the instrument to high heat conditions for a predetermined period of time in order to kill any bacteria or viruses which may adhere to the instrument during the previous treatment. However, the application of high heat to an electronically operated medical instrument, particularly a sophisticated medical instrument such as a laser optic system which conveys laser beams from a source to a patient, can cause stress in the material from which the instrument is made and shorten the useful life of the instrument, or possibly damage the electronics.

In addition, since prior art systems have involved the use of direct coupled, non-removable laser optic systems or non-disposable laser beam applicators which must be sterilized after use, the prior art sometimes requires the entire instrument, as opposed to just the laser optic system, to be subjected to the sterilization/autoclaving process. This can result in a large amount of stress being placed on the instrument, causing a considerably shortened useful life.

Prior art laser treatment devices that do not utilize a direct coupled optical system often include a sheathed and insulated optical rod assembly to convey the laser beam from the laser source to the patient undergoing treatment. A sheathed, insulated optical rod assembly represents an expensive, reusable system which requires sterilization between each use. Thus, if a doctor is going to treat multiple patients or multiple areas of the same patent, it is necessary to have a number of these expensive devices available in order to provide for continuous availability of the laser treatment system.

In addition, prior art systems for delivering low power laser beams typically include an expensive and complicated mirroring system for guiding the laser beam from the light source to the patient. Such a system increases the cost of the system and may be sensitive to the sterilization process, requiring adjustment or replacement after undergoing several sterilization procedures.

In addition to the problems associated with the sterilization process discussed above, a laser beam can present a hazard to the individual operating the device should the device be powered up without a laser guide in place to guide the laser beam. It is well known that laser beams, even low powered laser beams, can cause serious damage to an individual's eyes if the laser beam is mistakenly activated and the individual stares directly into the beam. Prior art laser systems which are capable of being powered up without a laser beam optical system in place to guide the generated laser beam pose a particular hazard in this regard. In addition, prior art laser systems have collimating lenses which focus the laser beam and which create a further hazard to retinal tissue. An individual operating the system may inadvertently power the system up in the process of preparing the system for use without a guide in place. This can result in the individual's retina, a patient or other person nearby, being exposed to an uncontrolled and dangerous level of laser beam energy.

Accordingly, there is a need for a laser beam application system which obviates the above and other problems, and which is disposable, inexpensive, and yet capable of conveying a laser beam from a laser beam source to a patient in a manner which ensures that proper energy output is present at the treatment end of the laser beam delivery system in order to appropriately treat a patient's needs while at the same time protecting the operator or patient from retinal damage caused by accidental exposure to the laser beam.

SUMMARY OF THE INVENTION

The present invention provides for a laser treatment system having a laser beam application device which is disposable, economical, and which provides additional safety features to avoid unnecessary exposure of individuals to laser beam energy. Instead of requiring the sterilization of the entire instrument or the laser beam applicator as with the prior art, the laser beam applicator system of the present invention can be removed from a laser beam generating device and disposed of after use. A new applicator can immediately be placed on the laser beam generator for treatment of a subsequent patient or for use on another body area of the same patient.

In addition, the present invention provides a solution for eliminating the inadvertent generation of laser beams when a laser beam applicator is not present on the laser beam generator. This safety feature assists in avoiding the unnecessary and often harmful exposure caused by laser beams generated without a laser beam applicator properly in place on the instrument.

Further, the system of the present invention does not require a collimating lens to focus the laser beam. This not only reduces the cost of the present invention, it also reduces or eliminates the hazard to an individual's retinal tissues.

The above and other features of the present invention will become more apparent upon a reading of the detailed description of the present invention taken in conjunction with the figures of which the following is a brief description.

BRIEF DESCRIPTION OF THE DRAWINGS

FIG. 7 is a side cut away view of a fiber optic assembly in accordance with the present invention;

FIG. 8 shows in block diagram form a circuit for generating a laser beam in accordance with the present invention.

DETAILED DESCRIPTION OF THE PREFERRED EMBODIMENT

Figure 1:
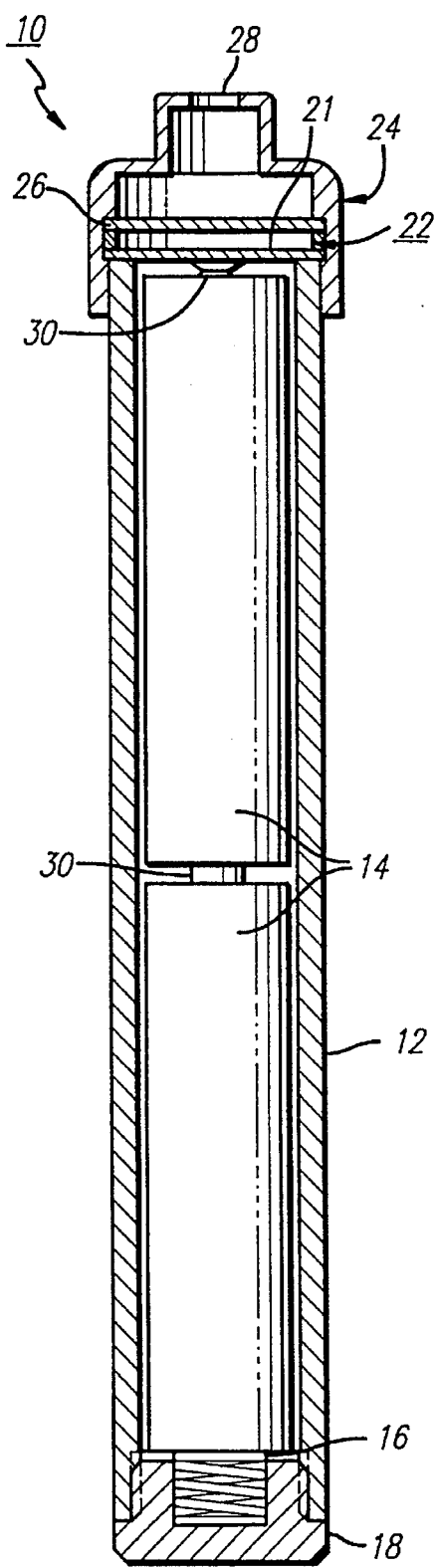
FIG. 1 is a side cutaway view showing a hand-held laser pen assembly in accordance with the present invention.
Figure 2:
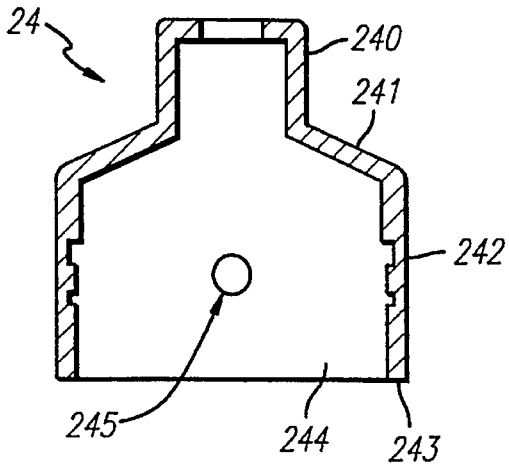
FIG. 2 is a detailed view of the end cap on the laser pen assembly shown in FIG. 1.
Figure 3:
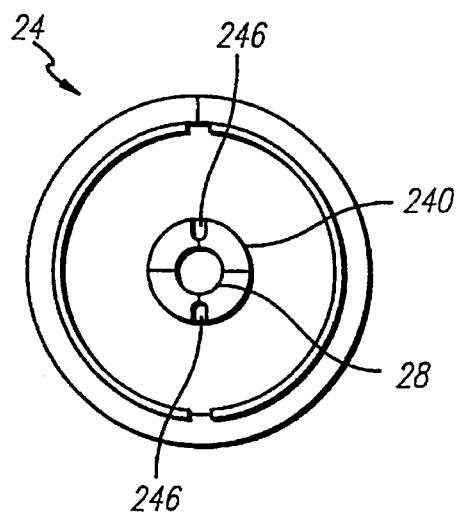
FIG. 3 is a top view of the end cap shown in FIG. 2.
Figure 4:
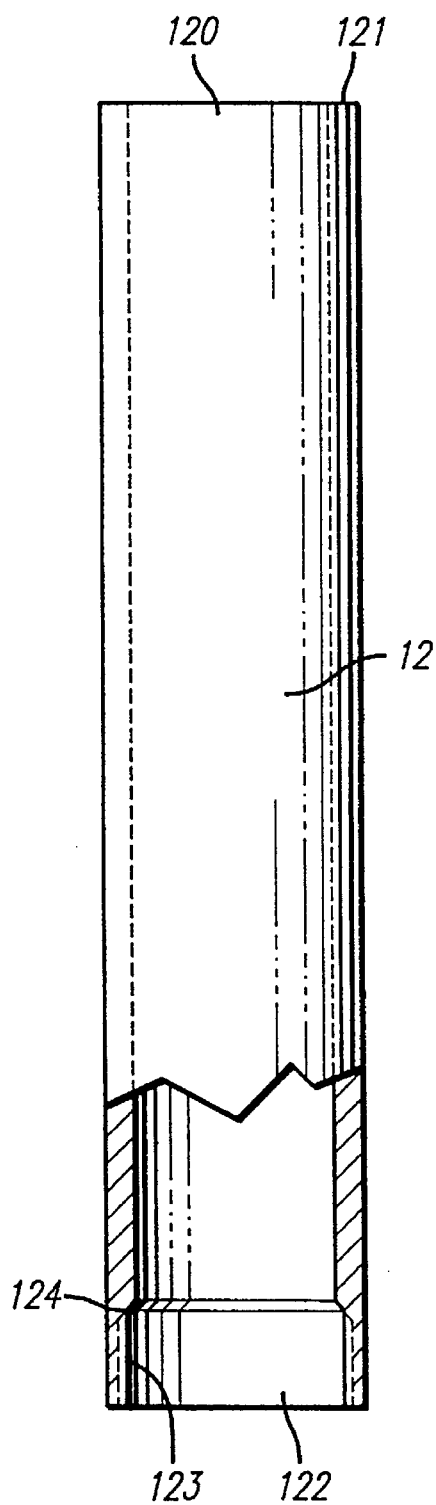
FIG. 4 is a partial side view of the outer case of the laser pen assembly shown in FIG. 1.
Figure 5:
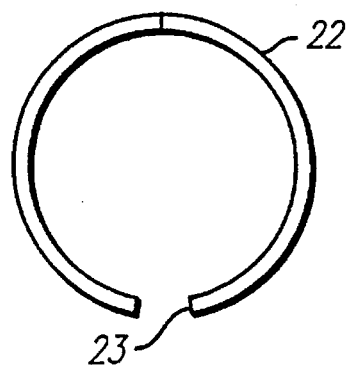
FIG. 5 is a top view of the spacer for the laser pen assembly shown in FIG. 1.
Figure 6:
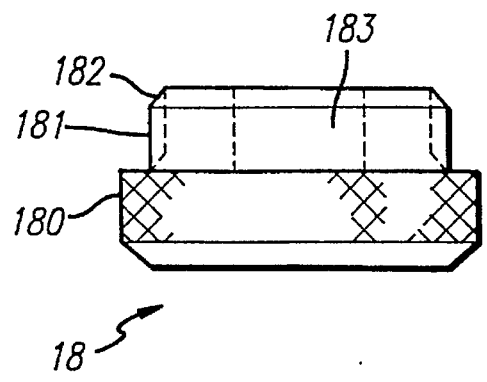
FIG. 6 is a side view of a cap for the laser pen assembly shown in FIG. 1.

FIGS. 1-6 show a laser pen assembly for use with the present invention. While the present invention is not limited to use with a hand-held laser pen assembly such as that shown in the drawings, the application of laser beam energy for wound healing, pain reduction and nerve stimulation typically involves the use of a low-power laser diode having an output on the order of five to 30 milliwatts. Such a laser does not require a large power supply and can be conveniently carried by an attending physician in the form of the laser pen shown in the figures. However, it should be understood that the present invention is applicable for use with other sources of laser beams, including laser beam generators of higher power than 5-30 milliwatts.

A laser pen assembly in accordance with the present invention includes a laser pen 10, having an outer case 12 which can be made of aluminum tubing. The outer case contains batteries 14 having a plurality of battery contacts 30. The batteries 14 may comprise standard alkaline batteries of suitable size. Although the FIGURE shows two batteries, the outer case 12 may be sized to fit any desired number of batteries (e.g., 3 or 4). A spring 16 is seated in a bottom cap 18. Spring 16 provides a force sufficient to bias the batteries 14 so that the terminals 30 make sufficient and consistent contact.

End cap 24 mounts via a slip fit over the circuit boards 26 and power terminal 21. The end cap 24 includes a nipple portion 240, an angled or flat recessed surface portion 241 and a side surface 242. The inner diameter of the side surface 242 is preferably sized so as to mate with the outer diameter of the outer case 12.

End cap 24 is provided with a hole 245 formed therein for provision of a light emitting diode (LED) which is electrically connected to the circuit board 26 to provide a visible exterior indication of the power-ON and power-OFF state of the laser pen. As can be seen in more detail in FIG. 3, a pair of electrical contacts 246 are provided in an upper surface of the end cap 24. The pair of electrical contacts are electrically connected to the circuit board 26 and constitute a safety feature which will be discussed in more detail below.

Spacer 22, which separates the circuit board 26 from the power terminal 21, is provided with a slot 23 formed therein which allows the LED to be placed between the circuit board 26 and the power terminal 21 and to appear through the opening 245 formed in the end cap 24.

Cap 18 which is disposed on the bottom end of the laser pen assembly 10 includes a knurled exterior surface portion 180 which allows for easy gripping of the cap 18. A threaded portion 181 is provided which mates in a screw fit with a threaded portion 123 on an interior surface of the outer casing 12. The cap 18 can be unscrewed to allow easy access to the interior of the outer casing 12 for replacement of the batteries 14.

The outer casing 12 is provided with an angled surface 124 disposed at a top portion of the threads 123 which mates with a similarly angled portion 182 on the cap 18. This acts as a limiter for limiting the extent of travel of the cap 18 into the outer casing 12. A spring well 183 is provided in the cap 18 for containing the spring 16 shown in FIG. 1. The spring 16 may be permanently attached to the cap 18 by way of a soldered fit or any other suitable means for attaching the spring 16 to the cap 18, or the spring may simply rest in the well and be held in place by pressure against the batteries. The spring is sufficiently tensioned to positively bias the batteries 14, thereby ensuring consistent connections between the batteries 14 and the battery terminals 30.

Although the laser pen assembly shown in FIGS. 1-6 provides an appropriate laser beam for medical purposes, it is still necessary to provide a device for conveying the generated laser beam from the laser pen assembly to a patient undergoing treatment.

FIG. 7 shows a fiber optic assembly 40 for conveying a laser beam generated by the laser pen assembly shown in FIGS. 1-6 to a patient undergoing treatment. The fiber optic assembly 40 includes an optical rod 400 which is supported by an optical rod support 401. The optical rod 400 can be a standard fiber optic strand made of glass or other suitable material for conveying laser beams. Such rods are well known and are manufactured by, for example, DuPont Corporation and Mitsubishi Electric Corporation. The optical support 401 is preferably made of plastic such as Delrin, but may also be made of rubber or some other suitable material capable of supporting the optical rod 400 and being sterilized. All components can be bonded with an epoxy based adhesive, or any other adhesive suitable for medical applications.

Mated with the optical support 401 in the inner cavity 403 is a conductive surface 402. The conductive surface may be formed integral with the optical support 401 during the molding of the optical support 401 or may consist of a conductive washer made from, for example, brass or stainless steel, which is disposed in the inner cavity 403. Such a washer would have a passage way therethrough in order to allow the optical rod 400 to protrude through the washer into the inner cavity 403 and would preferably be bonded to the optical support 401.

The fiber optic assembly 40 is mated with the laser pen assembly 10 shown in FIGS. 1-6. Referring in particular to FIGS. 1 and 7, the fiber optic assembly 40 would be placed over the nipple portion 240 of the end cap 24 and held in place via a friction fit created between the sidewalls 404 of the optical support 401 and the surface 240 of the end cap 24. The end cap 24, which may be made from aluminum, stainless steel or other suitable material, may be provided with a finish which assists in creating a greater friction fit between the optical support 401 and the end cap 24.

The optical rod 400 has ground and polished ends 406 and 407. A portion of the optical rod 405 protrudes through the optical support 401 to an inner cavity 403 which is defined by lateral side walls 404 of the optical support 401.

When placed in proper position over the end cap 24, the protruding portion 405 of the optical rod 500 extends through the opening 28 formed in the end cap 24 and interfaces with the face of the laser diode disposed on the circuit board 26. The laser diode (not shown) is positioned on the circuit board 26 such that the polished end surface 407 of the optical rod 400 is positioned directly adjacent to the laser diode disposed on the circuit board 26. When the laser diode generates a laser beam, it immediately enters the optical rod through the polished end 407, travels through the optical rod 400 and exits the optical rod through the polished end 406. Thus, in use, the laser pen assembly 10 with the fiber optic assembly 40 attached thereto would be utilized by an attending physician to treat a patient with the laser beam which exits the polished end 406 of the optical rod.

It should be well understood that the present invention is in no way limited to the configuration of the optical rod shown in FIG. 7. While FIG. 7 shows the optical rod having a bend therein, and such a bend would be useful for applications which require the laser beam to be applied to surfaces which may not be readily available using a straight optical rod 400 (e.g., oral applications, or other treatments in body orifices), the optical rod may be designed with any desired shape and is not limited to the curved optical rod shown in the FIGURE.

A significant feature of the optical rod 400 shown in FIG. 7 is the ability of the rod 400 to conduct a laser beam directly from the laser diode on the circuit board 26 and allow the laser beam to exit the polished end 406 with sufficient energy for medical purposes. The prior art requires the use of a collimating lens to achieve a laser beam having sufficient focused energy to achieve proper absorption or depth of penetration. However, after conducting extensive research, the inventor determined that a collimating lens was unnecessary. By properly situating the optical rod 400 against the face of the laser diode, the resultant laser beam output from the polished end 406 contains sufficient energy for medical purposes, including absorption and depth of penetration. In addition, the elimination of the collimating lens together with the use of a low power 5 milliwatt laser diode removes the hazards associated with the use of a focused beam and the corresponding regulations associated therewith.

For example, if a physician requires a laser beam having an energy content of substantially five milliwatts, it is necessary for the laser beam exiting the polished end 406 to have a strength equal to substantially five milliwatts of energy. In this regard, the optical rods used with the present invention are selected to provide for minimal energy loss of the laser beam produced by the laser diode. Thus, if, for example, a five milliwatt laser diode is utilized, by properly positioning the rod 400 relative to the laser diode, the rod 400 will receive substantially all of the laser beam energy generated by the diode and the laser beam exiting the polished end 406 of the optical rod 400 will contain substantially five milliwatts of energy.

In this regard, the inventor has studied the benefit of providing the optical rod 400 with insulation and sheathing as is present in the prior art. In experiments conducted, the inventor found that, with a five milliwatt laser diode being employed, the laser beam exiting the polished end 406 contains substantially 5 milliwatts of power. In other words, the strength level of the exiting laser beam was well within acceptable limits for use in medical treatments employing a laser diode of this type. For low powered laser treatments, providing for a sheathed and insulated optical rod was found to be unnecessary and merely served to increase the overall cost of the fiber optic assembly with no corresponding increase in operational efficiency. This is also true with respect to the use of the collimating lenses of the prior art.

In addition, benefits of cost savings are obtained through reduced down time by not having to wait for sterilization procedures. In addition, the treating physician can be certain of not transmitting AIDS, hepatitis, herpes and other communicable viruses through improper sterilization, especially when the instrument is used to treat open wounds such as ulcers or in body cavities.

A substantial benefit of the fiber optic assembly such as 40 shown in FIG. 7, is that such assemblies can be manufactured and distributed as pre-packaged, pre-sterilized, disposable, one-time use assemblies. An attending physician would simply attach the fiber optic assembly desired to the laser pen assembly 10 to treat a patient. Once the treatment is complete, the physician would remove the fiber optic assembly 40, dispose of the used assembly and, if necessary, attach a new assembly 40 to the laser 10 to complete additional treatments. In this manner, it is unnecessary for the entire laser instrument including the laser pen 10 to be subjected to a sterilization process.

An added benefit of the present invention is the ability to comply with the Occupational, Safety and Health Administration (OSHA) regulations on sterilization of medical instruments. When using the present invention, considering the single use, pre-sterilized status of the fiber optic assemblies disclosed above, the physician can be assured that each new assembly is fully guaranteed to be completely virus and bacteria free. The manufacturing site can be monitored to comply with OSHA regulations, and the physician is freed from the responsibility of monitoring the sterilization process to ensure compliance with such regulations.

FIG. 8 shows in general block diagram form the use of the conductive surface 402 on the optical support 401 to control the generation of the laser beam by the laser beam generating circuit. Electronic circuits for generating a laser beam using a laser diode are known. The present invention is not limited to use with a particular laser beam generating circuit, although the preferred form for such a circuit is discussed in more detail below with respect to FIG. 12. In the preferred embodiment, the present invention is intended for use with low power medical lasers having an output power on the order of 5–30 milliwatts which have gained wide acceptance in the medical field for wound healing, pain reduction and nerve stimulation.

The laser beam circuit 500 includes a laser beam generating circuit 501 including a laser diode 503. A power supply (i.e., batteries 14 shown in FIG. 1) is provided which connects with a first one of the terminals 246 provided on the upper surface of the end cap 24. A second one of the pair of terminals 246 is connected with lead 504 which connects with the laser beam generating circuit 501. In this manner, until a fiber optic support 401 with the conductive inner surface 402 is properly seated on the end cap 24, the connection between the terminals 246 will not be completed and power will not be supplied to the laser beam generating circuit 501, thus preventing the generation of the laser beam by laser diode 503.

It should be noted that as shown in FIG. 8, when the fiber optic support 401 is properly seated on the end cap 24, the fiber optic rod 400 is positioned directly adjacent the laser diode 503 and receives the laser beam generated thereby.

Alternatively, the treating physician may desire to use the present invention without the fiber optic rod 400. In this case, a conductive cream may be used on the patient, and the end cap can then be applied directly to the patient's body. The cream would then complete the connection between the pair of terminals 246 and the laser diode 503 would be capable of generating a beam. However, if this technique is used, it would then be necessary to sterilize the entire instrument, thus eliminating the benefits associated with the use of the single-use, disposable, pre-sterilized fiber optic assemblies discussed above.

As discussed above, inadvertent generation of laser beams can cause serious retinal injuries to both medical personnel and patients. The conductive surface 402 on the optical support 401 operates as a safety switch to prevent the inadvertent generation of laser beams without a fiber optic assembly in place. The pair of electrical contacts 246 disposed on the upper surface 240 of the end cap 24 represent a break in the circuit which ultimately supplies power to the laser diode. If the connection between the two contacts 246 is not completed using a conductive surface, the laser pen 10 will not generate a laser beam. Thus, the laser pen assembly 10 shown in FIGS. 1–6 will not be capable of providing a laser beam output until the fiber optic rod assembly with the conductive inner surface 402 is in proper place on the end cap 24.

Through the use of the conductive inner surface 402, the present invention assists in avoiding accidental activation of the laser pen assembly 10 by requiring that the fiber optic assembly 40 first be properly seated on the instrument before the instrument can be turned on. In addition, the provision of a flashing indicator through hole 245 provides an additional indication to the user of the instrument that the device is turned on and that care should be exercised to avoid any unnecessary exposure to the laser beam by the operator or patient's retina. In this manner, the present invention facilitates the safe and effective operation of the laser pen assembly 10 shown in FIGS. 1–6.

In addition, the elimination of the collimating lens provides a second safety feature that reduces the hazards that are associated with a focused laser beam. While the fiber optic assemblies of the present invention are certainly capable of be used with a laser having a collimating lens, in the preferred embodiment of the present invention the collimating lens is unnecessary. Particular applications may, however, require the use of a focused beam and it should be clear that the fiber optic assembly of the present invention is quite capable of working with such laser beams.

The fiber optic assembly 40 need not be limited to a the use of a single fiber optic rod 400 as shown in FIG. 7. More particularly, as can be seen in FIGS. 9–11, the fiber optic assembly may take a variety of configurations depending upon the type of treatment for which the laser assembly 10 is to be utilized.

Figure 9:
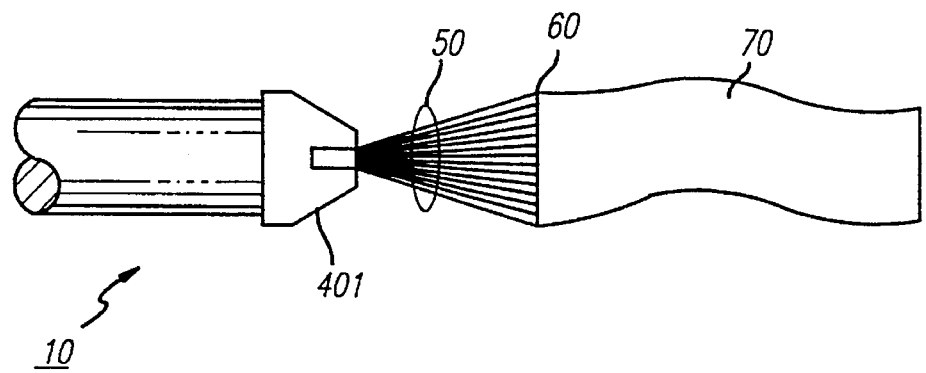
FIG. 9 is a side view of a wound healing bandage in accordance with the present invention.

Referring to FIG. 9, the laser assembly 10 has the fiber optic support 401 disposed thereon and a plurality of fiber optic strands 50 exit from the fiber optic support 401. The strands 50 are attached to a wound healing bandage 70 at a bonding point 60. The bandage 70 may be comprised of a thin, plastic, flexible, energy conducting sheet which leaks the laser energy output from the plurality of fiber optic strands 50 over a wide range for treating larger wounds. The wound healing bandage 70 must be abraded or hot stamped on the surface thereof in order to cause the energy supplied by the plurality of fiber optic strands 50 to leak out of the bandage to the wound treatment area. If not, the bandage 70 would act as a "light guide" and allow the energy produced from the fiber optic strands 50 to exit via the end of the bandage 70.

To cause the laser beam energy produced by a laser diode to enter the fiber optic strands and be disbursed and distributed therethrough, the ends of the fiber optic strands 50 which are inserted into the optical support 401 are first bonded together to form an integral structure. Then, the bonded structure is cut and polished at the end thereof so that the fiber optic bonded structure which is inserted into the support 401 is an even, integral structure which abuts the laser diode in the same fashion as the optical rod 400 shown in FIG. 7. Thus, the laser beam generated by the laser diode is automatically disbursed in appropriate amounts to the plurality of fiber optic strands 50 and is then conducted accordingly to the bandage 70.

Figure 10:
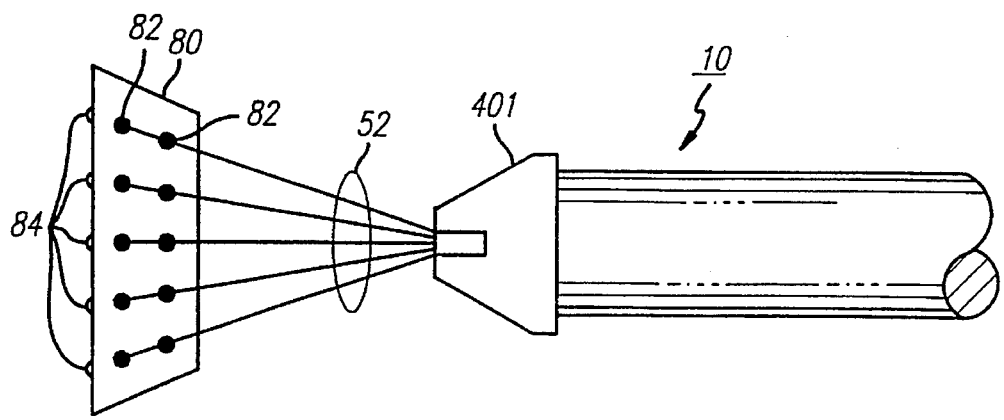
FIG. 10 is a side view of a wound healing applicator in accordance with the present invention.
Figure 11:
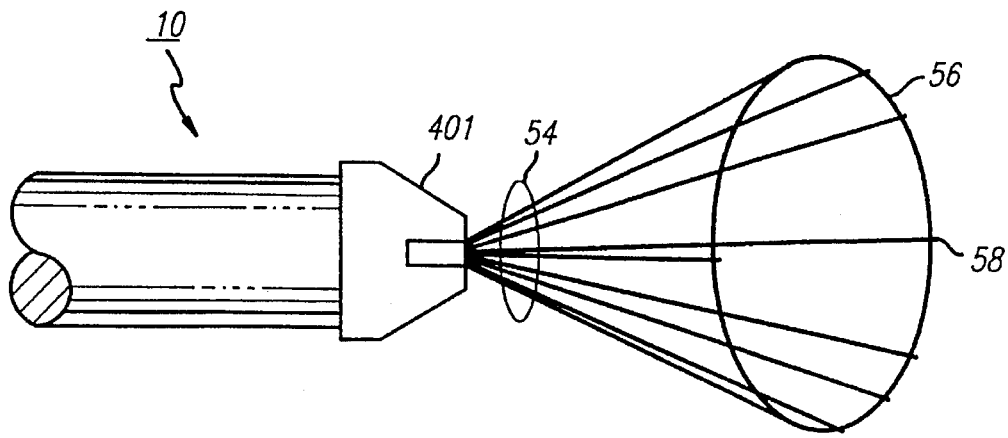
FIG. 11 is a side view of a fiber optic assembly for treating a wound area in accordance with the present invention.

FIG. 10 shows a thin flexible plastic sheet 80 which receives a plurality of fiber optic strands 52 which are formed in a fashion similar to those discussed above with respect to FIG. 9. The plurality of fiber optic strands 52 are matched with holes 82 formed in the plastic sheet 80 and exit the plastic sheet by a predetermined amount such that a polished and ground end 84 protrudes from an under side of the plastic sheet 80. The ends of the fiber optic rods 52 are heated and rounded to create in essence many convex lenses to create a convex lens effect. Laser energy exits the strands out of the convex lens and can be applied to an appropriate treatment area on a patient. Preferably, two fiber optic strands are provided through each hole 82 formed in the plastic sheet 80. The plastic sheet 80 can be bonded to the fiber optic strands 52 and allow an appropriate amount of fiber optic strand to exit through the under side of the plastic sheet 80.

A further embodiment shown in FIG. 11 includes a plurality of fiber optic strands 54 which are bonded, cut, polished and inserted into the optical support 401 in the same manner as those embodiments shown in FIGS. 9 and 10. In the embodiment shown in FIG. 11 a plurality of fiber optic strands 54 are spread and bonded to a plastic ring 56. The plurality of strands 54 have polished and rounded ends to also create a convex lens effect in the manner discussed above with respect to FIG. 10. The plastic ring 56 provides for a proper spread of the fiber optic rod 54 such that the ring can be applied over a wound area in order to treat the area defined by the plastic ring 56. The plastic ring 56 can be made in any desired size in order to treat various sizes and types of wounds. Such an instrument would suitable for treating localized wounds such as ulcers, various lesions, herpes sores and various localized infections.

In each of the embodiments shown in FIGS. 9–11, the system can use a laser diode of greater strength than the five milliwatt diode discussed above. For example, a 30 milliwatt laser diode could be used. In this case, a generated beam would be disbursed over the plurality of fiber optic rods, with each rod outputting a laser beam having less power than the 30 milliwatt total power of the beam output from the laser diode.

Figure 12:
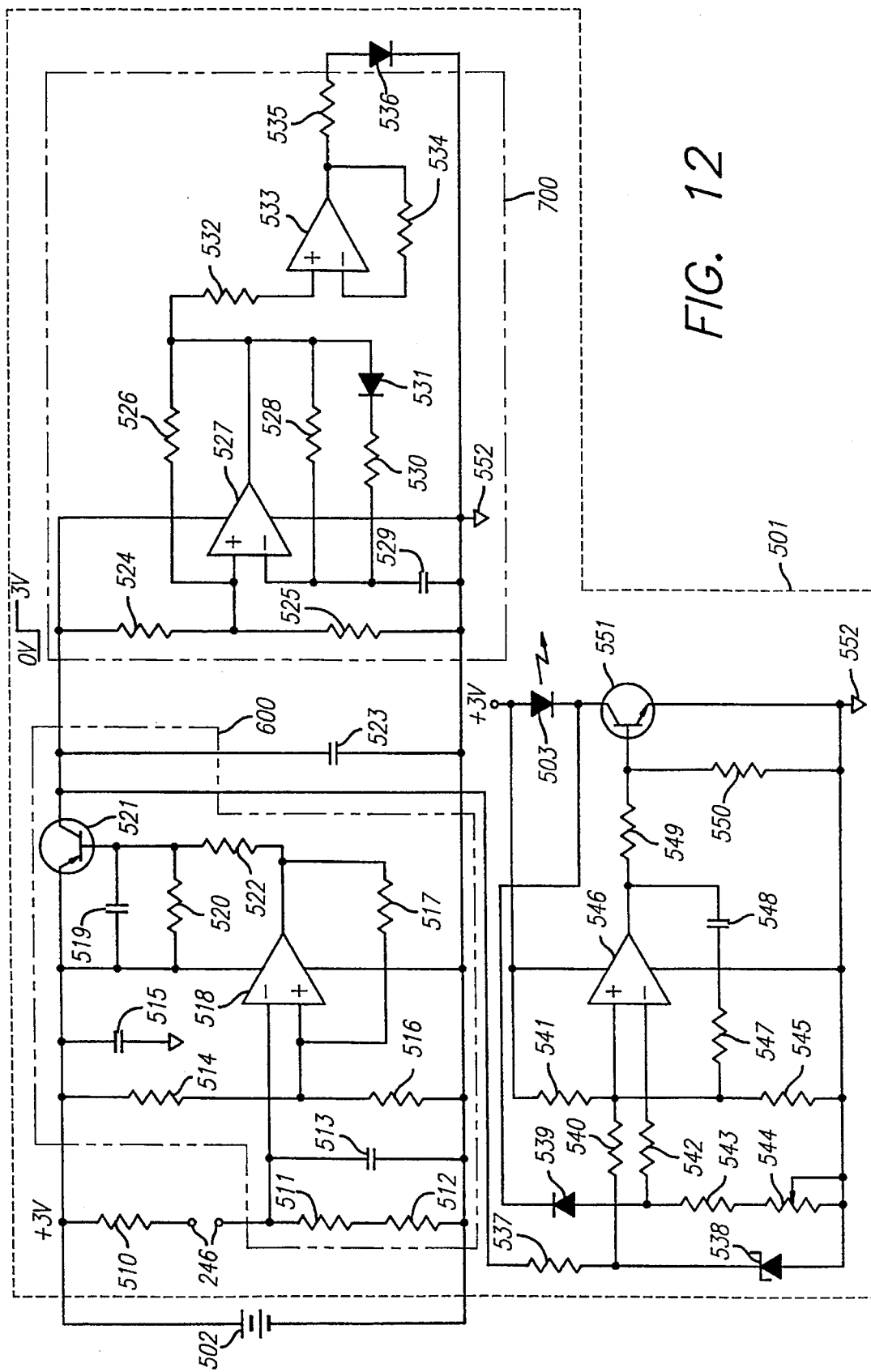
FIG. 12 is a schematic diagram showing a preferred embodiment of the laser beam generating circuit shown in FIG. 8.

FIG. 12 shows a preferred laser beam generating circuit for use with the present invention.

The laser beam generating circuit 501 is supplied with power from a power supply 502. The power supply may comprise, for example, two to three battery cells such as size AA alkaline batteries or other suitable batteries. The batteries may also be of the rechargeable, nickel cadmium type and the total voltage supplied by power supply 502 is preferably between 3 and 4.5 volts. The details of the laser beam generating circuit would be readily understandable by one skilled in the art. However, for completeness the following description is provided.

The power supply 502 is connected to a resistor 510, which is preferably 20 Ω and which is used to limit the current during battery charging. The pair of electrical contacts 246 immediately follow the resistor 510. The electrical contacts 246 are those which appear at the top of the end cap 24. The circuit shown in FIG. 12 will not operate without providing a connection between the pair of electrical contacts 246. Thus, the pair of electrical contacts 246 serve as a switch to prevent the inadvertent operation of the laser beam generating circuit 501. In addition, the contacts 246 can be used to charge the batteries 14.

Connected to the lower contact 246 is a subcircuit denoted by dashes and dots and identified by the reference numeral 600. This subcircuit 600 serves to switch battery power to the other portions of circuit 501 when a connection is made between electrical contacts 246. Subcircuit 600 includes resistors 511 and 512 which are preferably 10 MΩ and which are connected in parallel with a 0.1 μf capacitor 513. Capacitor 513 is used to hold the laser circuit 501 ON for two to three seconds after the electrical contacts 246 open.

Resistor 514, preferably 20 kμ, is connected with a 10 kΩ resistor 516. Tied between the two resistors 514 and 516 is an input to integrated circuit 518 which may comprise an integrated circuit such as that manufactured by National Semiconductor, Part No. LMC6482IM. The other input to the integrated circuit 518 is tied to capacitor 513 and resistor 511. A 0.1 μf capacitor 515 is connected to ground between resistor 514 and the emitter of transistor 521. Transistor 521, which is a PNP transistor, has a 0.1 μf capacitor 519 and a 51 kΩ resistor 520 tied between its base and emitter. A 1 kΩ resistor 522 is tied between the output integrated circuit 518 and the base of transistor 521. A 270 kΩ resistor 517 is tied between the positive input of integrated circuit 518 and the output thereof. A 0.1 μf capacitor 523 is tied between the collector of transistor 521 and ground 552.

Another subcircuit of circuit 501 has been set apart by dashed lines and double dots and identified by reference numeral 700. Subcircuit 700 includes two integrated circuits 527 and 533 which are identical to 518 discussed above. While one skilled in the art would readily understand from the FIGURE the operation of subcircuit 700, integrated circuit 527 and the components related thereto form a free-running pulse generator which generates approximately one to two pulses per second. Integrated circuit 533 serves as a buffer amplifier to provide sufficient current to pulse the LED 536. The LED 536 is visible through the hole 245 formed in the end cap 24 to provide the user with an indication as to the power-ON and power-OFF condition of the laser beam generating circuit 501.

Resistors 524, 525 and 526 are preferably 1 MΩ resistors, resistor 528 is preferably 5.1 MΩ, capacitor 529 is preferably 0.5 μf, resistor 530 is preferably 10 kΩ and diode 531 is a standard diode such as Part No. IN4148 (ISS332 or 355), manufactured by Rohm. Resistor 532 and 534 are preferably 100 kΩ, resistor 535 is preferably 39 Ω and the LED 536 is a standard light emitting diode preferably red in color.

The remaining portion of the laser beam generating circuit 501 includes an integrated circuit 546 together with a transistor 551. Integrated circuit 546 is the same as circuits 518, 527 and 533 whereas transistor 551 is an a NPN transistor.

Integrated circuit 546 and the components related thereto are used as a comparator to compare a portion of the laser output power (which is the output of the PIN diode 539) with a fixed 1.2 volt voltage reference which is provided by the active zener diode 538. Diode 538 may comprise a National Semiconductor diode such as Part No. LM4041E1M3-1.2. The detected difference between the output of the PIN diode 539 and the 1.2 volt voltage reference is amplified in order to regulate the laser current to produce a 5 milliwatt laser beam.

Using the combination of diode 538 with the PIN diode 539 to regulate the power consumption of the laser diode 503 provides the present invention with excellent control over the power consumption of the circuit 501 since the laser diode is the largest power consumer in the circuit. By regulating the current in this fashion, the laser beam generating circuit 501 is able to provide a consistent laser beam for approximately 15–18 hours using two alkaline power cells. In contrast, prior art battery powered laser systems generally experience noticable laser beam energy drop off after one to two hours of use.

Variable resistor 544, which is preferably 100 Ω, is used to calibrate the laser diode 503 to provide a 5 milliwatt laser beam. Preferably, resistor 537 is 10 kΩ, resistor 540 is 51 kΩ, resistor 541 is 1 MΩ, resistor 542 is 10 kΩ, resistor 543 is 300 Ω, resistor 545 is 10 kΩ and resistor 547 is 1 kΩ resistor. Capacitor 548 is 0.1 μf and resistor 549 is 1 kΩ. Resistor 550 is 10 kΩ and transistor 551 is a NPN transistor, for example Part No. 2N3904. Laser diode 503 may comprise a Sony laser diode, Part No. SLD111 AV Laser Diode having a wavelength of 780 nanometers and a power output of 5 milliwatts. Other laser diodes having different power outputs may also be used with the present invention. Laser diodes having a larger power output may require minor changes to the circuit components.

While the above description of the circuit shown in FIG. 12 is general in nature, one skilled in the art would readily understand the operation thereof. Of course, the sizes of the resistors and capacitors could be changed without departing from the spirit and scope of the present invention, as could the types of integrated circuits and transistors. Furthermore, although the present invention is preferably used with the laser beam generating circuit shown in FIG. 12, the invention is in no way limited to use with such circuit.

In addition, one skilled in the art may determine another location for terminals 246 than the one shown. For example, it may be possible for terminals 246 to electrically isolate the laser diode 503 or to be provided in a different location to disable the laser beam generating circuit 501 until the optical support is mated with end cap 24. It is intended that all such variations fall within the scope of the present invention.

The present invention provides a system for delivering a laser beam to a patient during treatment that is cost effective and safe. The system is flexible and causes minimal wear and tear on the laser instrument due to eliminating the need for sterilization of the instrument after use. In addition, since the present invention uses pre-packaged, pre-sterilized fiber optic assemblies, the possibility that the system will suffer down time while waiting for a fiber optic assembly to be autoclaved/sterilized is also eliminated, ensuring one hundred percent availability of the laser treatment system.

For medical and dental applications, as discussed previously, the laser beam treatment system of the present invention is useful for pain control, wound healing, nerve stimulation, reduction of edema, and stimulation of the body's neurotransmitter and neurohormone systems. It also has application in the treatment of patients with transmissible diseases such as HIV, herpes, hepatitis, infections, as well as patients having open wound areas from surgical sites, ulcers, or various infections. It can be utilized in various bodily cavities or through skin contact alone and provide sufficient depth of penetration without using an excessively powerful laser diode. Once the treatment is completed, the fiber optic assembly may be disposed of in a safe and effective manner thereby eliminating the need to sterilize the entire instrument.

The present invention is no way limited to the embodiments discussed above. For example, it may be possible to include optical rods of many varying shapes and sizes depending upon the type of treatment being conducted. For example, an optical rod 400 can be provided with a ball on the tip thereof for use in sensitive body areas, thereby minimizing the pain caused by the application of the polished end 406 of the fiber optic rod 400 to the patient's body.

Alternatively, a pressure switch could be substituted for the terminals 246. The pressure switch would be activated when the optical support 401 was properly seated on the end cap 24, allowing the laser diode 503 to generate a laser beam. When pressure was removed from the switch, the circuit would open, and the laser beam generation would cease.

In addition to not being limited by the above discussed embodiments, the invention is no way limited to those shown in the drawings. The present invention is limited solely by the claims which are appended below.

I claim:

1. A laser beam therapy system comprising:

a laser beam generating circuit for generating a laser beam;

a housing having a first and second ends for containing said laser beam generating circuit, said first end being open and said laser beam generating circuit being disposed adjacent said first end;

an end cap mated with said first end, said end cap having an opening formed therein to allow said laser beam to pass therethrough and including a pair of electrical contacts disposed on an outer surface thereof, said pair of electrical contacts being electrically connected to said laser beam generating circuit for controlling the generation of said laser beam;

a fiber optic support mated with said outer surface of said end cap;

a fiber optic rod supported by said fiber optic support, said fiber optic rod mating with said opening formed in said end cap and extending into said first end of said housing adjacent said laser beam generating circuit to receive said laser beam when said fiber optic support is mated with said outer surface of said end cap; and switch means, disposed between said fiber optic support and said end cap, for completing a connection between said pair of electrical contacts, thereby enabling said laser beam generating circuit to generate said laser beam.

2. The laser beam therapy system according to claim 1, wherein said laser beam generating circuit includes a laser diode for generating said laser beam.

3. The laser beam therapy system according to claim 1, wherein said end cap includes a protuberance formed therein, said pair of electrical contacts being disposed on a surface of said protuberance.

4. The laser beam therapy system according to claim 3, wherein said optical rod support is comprised of a resiliently flexible material molded so as to mate in a friction fit with said protuberance.

5. The laser beam therapy system according to claim 4, wherein said switch means comprises a conductive material disposed on an inner surface of said optical rod support.

6. The laser beam therapy system according to claim 4, wherein said switch means comprises an electrically conductive washer placed between said optical rod support and said protuberance, said washer being positioned so as to contact said pair of electrical contacts when said optical rod support is mated with said protuberance.

7. A hand-held laser treatment system comprising:

a laser beam generating circuit for generating a laser beam;

a housing for containing said laser beam generating circuit, a first end of said housing being open so as to expose said laser beam generating circuit;

an end cap having an opening formed therein and mated with said first end;

a fiber optic support mated with said end cap;

fiber optic means extending through and supported by said fiber optic support, for conveying said laser beam generated by said laser beam generating circuit, said fiber optic means mating with said opening formed in said end cap and extending into said first end of said housing adjacent said laser beam generating circuit to directly receive said laser beam from said laser beam generating circuit; and means for controlling generation of said laser beam by said laser beam generating circuit.

8. The hand-held laser treatment system according to claim 7, wherein said fiber optic means comprises a plurality of fiber optic rods each having first and second ends, each of said plurality of fiber optic rods being bonded together at said first end so as to form a fiber optic bundle, said fiber optic bundle being ground and polished so as to form a substantially uniform, planar surface which is positioned adjacent said laser beam generating circuit when said fiber optic support is mated with said end cap.

9. The hand-held laser treatment system according to claim 8, wherein each of said plurality of fiber optic rods receives a portion of said laser beam generated by said laser beam generating circuit.

10. The hand-held laser treatment system according to claim 9, further comprising an energy conducting bandage adapted to receive and distribute laser beam energy over a surface thereof, wherein said second end of each of said plurality of fiber optic rods is bonded to said energy conducting bandage, said energy conducting bandage receiving the portion of the laser beam conducted by each of said plurality of fiber optic rods.

11. The hand-held laser treatment system according to claim 10, wherein said energy conducting bandage is comprised of plastic.

12. The hand-held laser treatment system according to claim 9, further comprising an applicator patch of a predetermined size having a plurality of openings formed therein, wherein said second end of each of said plurality of fiber optic rods passes through a corresponding opening in said applicator patch and protrudes a predetermined distance therethrough, said patch being bonded to plurality of fiber optic rods.

13. The hand-held laser treatment system according to claim 12, wherein each of said second ends of said plurality of fiber optic rods are rounded so as to create a plurality of convex lenses for applying said portion of said laser beam conducted thereby to a patient undergoing treatment.

14. The hand-held laser treatment system according to claim 13, wherein at least two fiber optic rods extend through each of said plurality of openings formed in said applicator patch.

15. The hand-held laser treatment system according to claim 9, further comprising optical rod distributing means, connected with said plurality of optical rods, for distributing said second end of said plurality of optical rods about a predetermined area.

16. The hand-held laser treatment system according to claim 15, wherein said distributing means comprises a ring formed of a resilient material bonded to said plurality of optical rods at a predetermined position, said ring defining said predetermined area.

17. The hand-held laser treatment system according to claim 16, wherein said second end of each of said plurality of optical rods extends a predetermined distance past said ring, and each of said second ends of said plurality of fiber optic rods are rounded so as to create a plurality of convex lenses for applying said portion of said laser beam conducted thereby to a patient undergoing treatment.

18. The hand-held laser treatment system according to claim 7, wherein laser beam generating circuit includes a laser diode for generating said laser beam.

19. The hand-held laser treatment system according to claim 7, wherein said means for controlling comprises:

a pair of electrical contacts for enabling and disabling said laser beam generating circuit, said pair of electrical contacts being disposed on said end cap and electrically connected to said laser beam generating circuit; and removable switch means, provided between said fiber optic support and said end cap, for providing an electrical connection between said pair of electrical contacts, thereby enabling said laser beam generating circuit.

20. The hand-held laser treatment system according to claim 19, wherein said removable switch means comprises an electrically conductive material disposed on an inner surface of said fiber optic support, said electrically conductive material completing an electrical connection between said pair of electrical contacts when said fiber optic support is mated with said end cap.

21. The hand-held laser treatment system according to claim 19, wherein said removable switch means comprises an electrically conductive washer disposed between said fiber optic support and said end cap, said washer completing an electrical connection between said pair of electrical contacts when said fiber optic support is mated with said end cap.

22. The hand-held laser treatment system according to claim 19, wherein said fiber optic support comprises a plastic cap bonded with said fiber optic means and molded so as to mate in a friction fit over said end cap, said removable switch means comprising an electrically conductive material disposed on an inner surface of said plastic cap which completes an electrical connection between said pair of electrical contacts when said plastic cap is mated with said end cap.

* * * * *